US00PP28540P3

(12) United States Plant Patent
Kordes

(10) Patent No.: US PP28,540 P3
(45) Date of Patent: Oct. 24, 2017

(54) HYBRID TEA ROSE PLANT NAMED 'KORCRIPOCO'

(50) Latin Name: *Rosa hybrida*
Varietal Denomination: KORcripoco

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 145 days.

(21) Appl. No.: 14/756,364

(22) Filed: Sep. 2, 2015

(65) Prior Publication Data

US 2017/0064890 P1 Mar. 2, 2017

(51) Int. Cl.
*A01H 5/02* (2006.01)

(52) U.S. Cl.
USPC ..... Plt./133

(58) Field of Classification Search
USPC ..... Plt./101, 130, 133
See application file for complete search history.

(56) References Cited

PUBLICATIONS

HelpMeFind website citation for 'Korcripoco'. https://www.helpmefind.com/rose/pl.php?n=97624. Accessed Mar. 20, 2017. 1 page.*

Rosenbaumschule website citation for 'Korcripoco'. http://www.rosenbaumschule.com/navi/shop/rosen/Edelrosen/Edelrose--Athena-----Korcripoco------Kordes--2014.html. Accessed Mar. 20, 2017. 2 pages.*

HelpMeFind website citation of 'Athena'.https://www.helpmefind.com/rose/l.php?l=2.379.0. Accessed Mar. 20, 2017. 1 page.*

* cited by examiner

*Primary Examiner* — Susan McCormick Ewoldt
*Assistant Examiner* — Karen Redden
(74) *Attorney, Agent, or Firm* — Samuel R. McCoy, Jr.

(57) ABSTRACT

'KORcripoco' is a new and distinct variety of *Rosa hybrida* which is characterized by the combination of an upright growth habit and large, very-double flowers with cream centers and pink edges. The new variety propagates successfully by grafting and by stem cuttings and has shown to be uniform and stable in the resulting generations from asexual propagation.

1 Drawing Sheet

Latin name of genus and species: The Latin name of the genus and species of the novel variety disclosed herein is *Rosa hybrida*.

Variety denomination: The inventive variety of *Rosa hybrida* disclosed herein has been given the variety denomination 'KORcripoco'.

BACKGROUND OF THE INVENTION

The present invention relates to a new and distinct *Rosa hybrida*, hybrid tea rose cultivar, which has been given the variety denomination of 'KORcripoco'. Its market class is PLT/130.

Parentage: The *Rosa hybrida* variety 'KORcripoco' is the result of a controlled cross-pollination breeding program carried out by the inventor in Offenseth-Sparrieshoop, Germany. The objective of the said breeding program was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORcripoco' from all other varieties known to the inventor.

'KORcripoco' is a seedling selection which resulted from the controlled pollination of an unnamed breeding line developed and owned by the same inventor, the seed parent, and *Rosa hybrida* 'KORquelda' (U.S. Plant Pat. No. 17,048), the pollen parent, during the summer of 2002.

As part of a rose development program, Tim-Hermann Kordes germinated seeds from the aforementioned hybridization during the following winter and conducted evaluations and observations on the resulting seedlings in a controlled environment in Offenseth-Sparrieshoop, Germany. The resulting seedlings exhibited distinctive physical and biological characteristics. The new rose plant was selected as a single plant in May of 2003 from the seedling beds due to its superior characteristics and asexually propagated for further evaluation. This new and distinctive rose variety was given the name 'KORcripoco'.

Asexual Reproduction: The first asexual propagation of 'KORcripoco' was performed in July of 2003 at the inventor's nursery in Offenseth-Sparrieshoop, Germany. Subsequently, 'KORcripoco' has been successfully propagated by stem cuttings and grafting in Jackson County, Oreg. These initial and other subsequent propagations conducted in controlled environments demonstrate that 'KORcripoco' reproduces true to type in successive generations of asexual reproduction.

SUMMARY OF THE INVENTION

The following characteristics have been repeatedly observed and represent the distinguishing characteristics of the new *Rosa hybrida* cultivar 'KORcripoco'. These traits, in combination, distinguish 'KORcripoco' as a new and distinct cultivar.

1. *Rosa hybrida* 'KORcripoco' exhibits an upright growth habit; and
2. *Rosa hybrida* 'KORcripoco' exhibits an abundance of flowers born singularly and in clusters; and
3. *Rosa hybrida* 'KORcripoco' exhibits a very-double flower habit; and
4. *Rosa hybrida* 'KORcripoco' exhibits a large flower size; and
5. *Rosa hybrida* 'KORcripoco' exhibits flowers with cream-colored centers and pink edges, at anthesis; and
6. *Rosa hybrida* 'KORcripoco' exhibits very good disease resistance.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORcripoco', taken from plants of three years of age.

DETAILED BOTANICAL DESCRIPTION

The following is a detailed botanical description of a new and distinct variety of *Rosa hybrida* known as 'KORcripoco', based upon field observations made in June of 2015 from three year old plants, grown in-ground, at a nursery in Jackson County, Oreg.

Those skilled in the art will appreciate that certain characteristics will vary with older or, conversely, with younger plants. 'KORcripoco' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2001 edition except where common terms of color are used.

A botanical description of 'KORcripoco' and comparisons with other varieties of *Rosa hybrida* are provided below.

General plant description:

*Growth rate.*—Vigorous.

*Growth habit.*—Upright.

*Mature dimensions.*—Approximately 120 cm tall and 50 cm wide.

*Cold hardiness.*—Unknown. To date, the instant plant has been grown successfully in USDA Zone 7.

*Propagation.*—Grafting and stem cuttings.

*Disease resistance.*—Very good resistance to powdery mildew (*Sphaerotheca pannosa*), blackspot (*Diplocarpon rosae*) and rust (*Phragmidium* sp.) diseases under normal growing conditions in Jackson County, Oreg.

Root system: Fibrous.

Stems:

*Stem color.*—Mature stems are Yellow-Green Group 146C.

*Stem surface texture.*—Smooth.

*Stem diameter.*—7 to 12 mm, on average.

*Prickles.*—Incidence — Average of 6 prickles per 10 cm of stem. Size — Average length is 10 to 15 mm. Immature prickle color — Greyed-Purple Group 187B. Mature prickle color — Yellow-Green Group 150C. Anthocyanin intonations — Greyed-Purple Group 187C present on mature prickles. Shape — Deeply concave. Texture — Smooth.

Leaves:

*Arrangement.*—Imparipinnate compound leaves; mature axillary leaves consisting of 5 leaflets.

*Attachment.*—Petiolate.

*Dimensions.*—135 to 140 mm long and 110 mm wide.

*Abundance.*—Very abundant.

*Stipules.*—Size — 25 to 30 mm long and 11 mm wide. Stipule color — Yellow-Green Group 144C. Anthocyanin intonations — Greyed-Red Group 182A; strong presence on the margins and faint presence on the adaxial surface of the midrib. Stipitate glands — Abundant; only present at margins. Margins — Cilliate. Texture, adaxial surface — Glabrous. Texture, adaxial surface — Glabrous. Apex — Apiculate. Base — Winged.

*Petiole.*—Length — Average 37 mm. Diameter — Average 1.5 mm. Petiole color, adaxial surface — Yellow-Green Group 144B. Petiole color, abaxial surface — Yellow-Green Group 145A. Margins — Entire with occasional presence of stipitate glands. Anthocyanin intonations — Greyed-Red Group 182A; strong presence on prickles and stipitate glands and faint presence on the adaxial surface of the midrib. Prickles — Few; 0 to 2 prickles on the abaxial surface. Stipitate glands — Limited number present on margins. Texture, adaxial surface — Glabrous. Texture, abaxial surface — Papillate. Strength — Strong.

*Rachis.*—Length — Average 17 mm. Diameter — Average 1.5 mm. Color — Yellow-Green Group 145A. Anthocyanin intonations — Greyed-Red Group 182A; present on prickles and stipitate glands. Margins — Entire with occasional presence of stipitate glands. Prickles — A few small prickles underneath. Stipitate glands — Limited number present on margins only. Texture, adaxial surface — Glabrous. Texture, abaxial surface — Papillate.

*Leaflets.*—Quantity — Normally 5 leaflets on normal leaves in middle of the stem. Dimensions — Average size of the terminal leaflet is 60 mm long and 35 to 40 mm wide. Shape — Elliptical. Apex — Cuspidate. Base — Obtuse. Margins — Serrated; slight undulation is occasionally present. Texture, adaxial surface — Semi-glossy and smooth. Texture, abaxial surface — Matte and leathery. Mature foliage color, adaxial surface — Green Group 137B. Mature foliage color, abaxial surface — Yellow-Green Group 147C. Anthocyanin intonations — None observed. Venation — Reticulate. Petiolule — Dimensions — 2 mm long and 1.5 mm in diameter. Petiolule color, adaxial and abaxial surfaces — Yellow-Green Group 145C. Anthocyanin intonations — Greyed-Red Group 182A present on stipitate glands. Prickles —

None present. Stipitate Glands — A few stipitate glands present along margins. Texture, adaxial and abaxial surfaces — Glabrous.

Inflorescence:

*Inflorescence type.*—Both corymbs with multiple flowers and solitary flowers observed.

*Blooming habit.*—Recurrent.

*Quantity of flowers.*—Generally 3 to 7 flowers on corymbs.

*Size.*—Corymbs are 250 to 290 mm tall and 150 to 200 mm wide, on average.

*Peduncle.*—Surface — Lacking stipitate glands. Length — 25 to 60 mm average length. Diameter — 4 to 6 mm average diameter. Color — Yellow-Green Group 144C. Anthocyanin intonations — Greyed-Purple Group 184C. Strength — Strong. Texture — Glabrous.

Flowering laterals: Present below the initiation of inflorescence. Generally 5 flowering laterals are present, with 1 flower per flowering lateral and 5 to 12 flowers per flower shoot.

Bud:

*Bud form.*—Pointed ovoid.

*Size.*—Upon opening, 40 mm in length from base of receptacle to distal end of bud and 30 mm diameter at its widest point.

*Texture.*—Leathery.

*Color, as sepals first unfold.*—Yellow-Green Group 145C with intonations of Red-Purple Group 58A.

*Color when one-quarter open, inner surface.*—Green-White Group 157A.

*Color when one-quarter open, outer surface.*—Green-White Group 157A, with a faint intonations of Red-Purple Group 58B along the margins.

*Color when one-quarter open, outermost petals.*—Yellow-Green Group 145C, with intonations of Red-Purple Group 58A.

Flower:

Pedicel:

*Surface.*—Pubescent with no stipitate glands.

*Length.*—140 to 190 mm, on average.

*Diameter.*—3 to 4 mm, on average.

*Color.*—Yellow-Green Group 144A.

*Anthocyanin intonations.*—Greyed-Purple Group 184C.

*Strength.*—Somewhat strong.

*Texture.*—Smooth.

Sepals:

*Diameter of calyx.*—75 to 85 mm, at anthesis.

*Quantity.*—Five.

*Color, adaxial surface.*—Yellow-Green Group 147C.

*Color, abaxial surface.*—Yellow-Green Group 146B.

*Anthocyanin intonations.*—Greyed-Red 182A.

*Size.*—40 mm long and 16 mm wide, on average.

*Shape.*—Weak foliaceous appendages on 3 of the 5 sepals.

*Apex.*—Cirrose.

*Base.*—Flat at union with receptacle.

*Texture, adaxial surface.*—Hoary.

*Texture, abaxial surface.*—Leathery.

*Margins.*—Cilliate.

*Stipitate glands.*—Limited; along margins.

Corolla:

*General shape of corolla.*—Rounded.

*Shape of corolla when viewed from the side.*—Upon opening, upper portion — Flattened convex. Upon opening, lower portion — Concave. Open flower, upper portion — Flat. Open flower, lower portion — Concave.

*Aspect.*—Flowers held upright.

*Dimensions.*—Large for a hybrid tea rose. When open, the average flower diameter is 90 mm and the average flower height is 50 mm.

*Fragrance.*—Light.

*Duration.*—On the plant 6 days. Senesced petals drop away cleanly.

*Petals.*—Petal arrangement — Not formal. Petal count — Exhibits very-double flowers with approximately 55 to 60 petals under normal conditions. Petal reflex — Outermost petals are slightly reflexed. Petal reflex occurs one by one. Petal margin — Ruffled. Petal shape — Orbicular, with some of the innermost petals obovate. Apex — Obtuse. Base — Obtuse. Dimensions — Approximately 35 to 55 mm long and 30 to 55 mm wide. Texture, inner surface — Smooth. Texture, outer surface — Smooth. Petal color, upon opening — Outermost petals, outer surface — Marginal zone — White Group 155B, with intonations of Red-Purple Group 58C. Middle zone — White Group 155B. Basal zone — White Group 155B. Outermost petals, inner surface — Marginal zone — White Group 155A, with intonations of Red-Purple Group 58C. Middle zone — White Group 155A. Basal zone — White Group 155A. Innermost petals, outer surface — White Group 155A. Innermost petals, inner surface — White Group 155A. Basal petal spots, upon opening — Basal petal spot, outermost petals — Dimensions — 3 mm high and 2 mm wide, on average. Color, outer surface — Yellow Group 3D. Color, inner surface — Yellow Group 3C. Basal petal spot, innermost petals — Dimensions — 3 mm high and 2 mm wide, on average. Outer surface — Yellow Group 3A. Inner surface — Yellow Group 3A. Petal color, after opening — Outermost petals, outer surface — Marginal zone — White Group 155B, with intonations of Red-Purple Group 58B. Middle zone — White Group 155B. Basal zone — White Group 155A. Outermost petals, inner surface — Marginal zone — White Group 155B, with intonations of Red-Purple Group 58B. Middle zone — White Group 155B. Basal zone — White Group 155A, with intonations of Red-Purple Group 58B. Innermost petals, outer surface — Marginal zone — White Group 155A. Middle zone — Yellow Group 8D. Basal zone — Yellow Group 8C. Innermost petals, inner surface — Marginal zone — White Group 155A. Middle zone — Yellow Group 8D. Basal zone — Yellow Group 8B. Basal petal spots, after opening — Basal petal spot, outermost petals — Dimensions — 3 mm high and 3 mm wide, on average. Color, outer surface — Not observed. Color, inner surface — Yellow Group 3C. Basal petal spot, innermost petals — Not observed. General Tonality — At anthesis, flowers are White Group 155B in the center and Red-Purple Group 58C at the edges of the corolla.

*Petaloids.*—*Quantity* — 10 to 15 petaloids per flower, on average. Dimensions — Approximately 10 to 30 mm long and 3 to 25 mm wide. Color, inner and outer surfaces — Marginal zone — Yellow Group 4D. Middle zone — Yellow Group 6D. Basal zone — Yellow Group 6A. Margins — Undulated and indented. Shape — Spatulate; many are highly irregular. Apex — Obtuse. Base — Attenuate. Texture, inner and outer surfaces — Smooth.

Reproductive organs:

Stamens:

*Quantity.*—Approximately 160, on average, and regularly arranged around the styles.

*Anthers.*—Dimensions — 2 to 4 mm long and 1 to 2 mm wide, on average. Color — Yellow-Orange Group 15D. Pollen — Abundant. Pollen Color — Yellow-Orange Group 22A.

*Filaments.*—Color — Yellow Group 4A. Length — 6 to 10 mm.

Pistils:

*Quantity.*—Abundant; approximately 120 present.

*Stigmas.*—Dimensions — 1 mm long and 1 mm wide. Location — Slightly inferior or equal to anthers. Color — Yellow Group 13C.

*Styles.*—Length — Approximately 5 to 7 mm long. Color — Yellow-Green Group 145D, with intonations of Red-Purple Group 58D.

Ovary:

*Dimensions.*—2 mm long and 1 mm in diameter.

*Color.*—Green-White Group 157A.

Receptacle:

*Shape.*—Funnel-shaped.

*Dimensions.*—Approximately 7 mm high and 10 to 12 mm wide.

*Surface.*—Glabrous and slightly glaucous.

*Color.*—Yellow-Green Group 144B.

*Texture.*—Smooth.

Hips and seed formation: Not observed.

COMPARISONS WITH THE PARENTS

The new rose plant may be distinguished from its seed parent, an unnamed seedling, by the following combination of characteristics:

1. 'KORcripoco' exhibits flowers with cream centers and pink edges, whereas the seed parent exhibits flowers with yellow centers and red edges.
2. 'KORcripoco' exhibits medium plant height, whereas the seed parent exhibits a tall plant height.

The new rose plant may be distinguished from its pollen parent, *Rosa hybrida* 'KORquelda', by the following combination of characteristics:

1. 'KORcripoco' exhibits flowers with cream centers and pink edges, whereas 'KORquelda' exhibits a yellow flower color.
2. 'KORcripoco' exhibits a more upright plant habit, whereas 'KORquelda' exhibits a more bushy habit.

COMPARISONS WITH SIMILAR *ROSA HYBRIDA* CULTIVARS KNOWN TO THE INVENTOR

For a comparison, several physical characteristics of the rose variety 'KORaruli', a rose variety from the same inventor described and illustrated in U.S. Plant Pat. No. 22,352 are compared to 'KORcripoco' in Chart 1.

CHART 1

| Characteristic | 'KORcripoco' | 'KORaruli' |
|---|---|---|
| General tonality of flower, at anthesis. | White Group 155B at the center and Red-Purple Group 58C at the edge. | Yellow Group 10B. |
| Petal count. | Approximately 55 to 60 petals under normal conditions. | Approximately 45 petals under normal conditions. |
| Bud color as sepals first unfold. | Yellow-Green Group 145C with intonations of Red-Purple Group 58A. | Yellow-Orange Group 23B. |

That which is claimed:

1. A new and distinct variety of rose plant named 'KORcripoco', as described and illustrated herein.

* * * * *

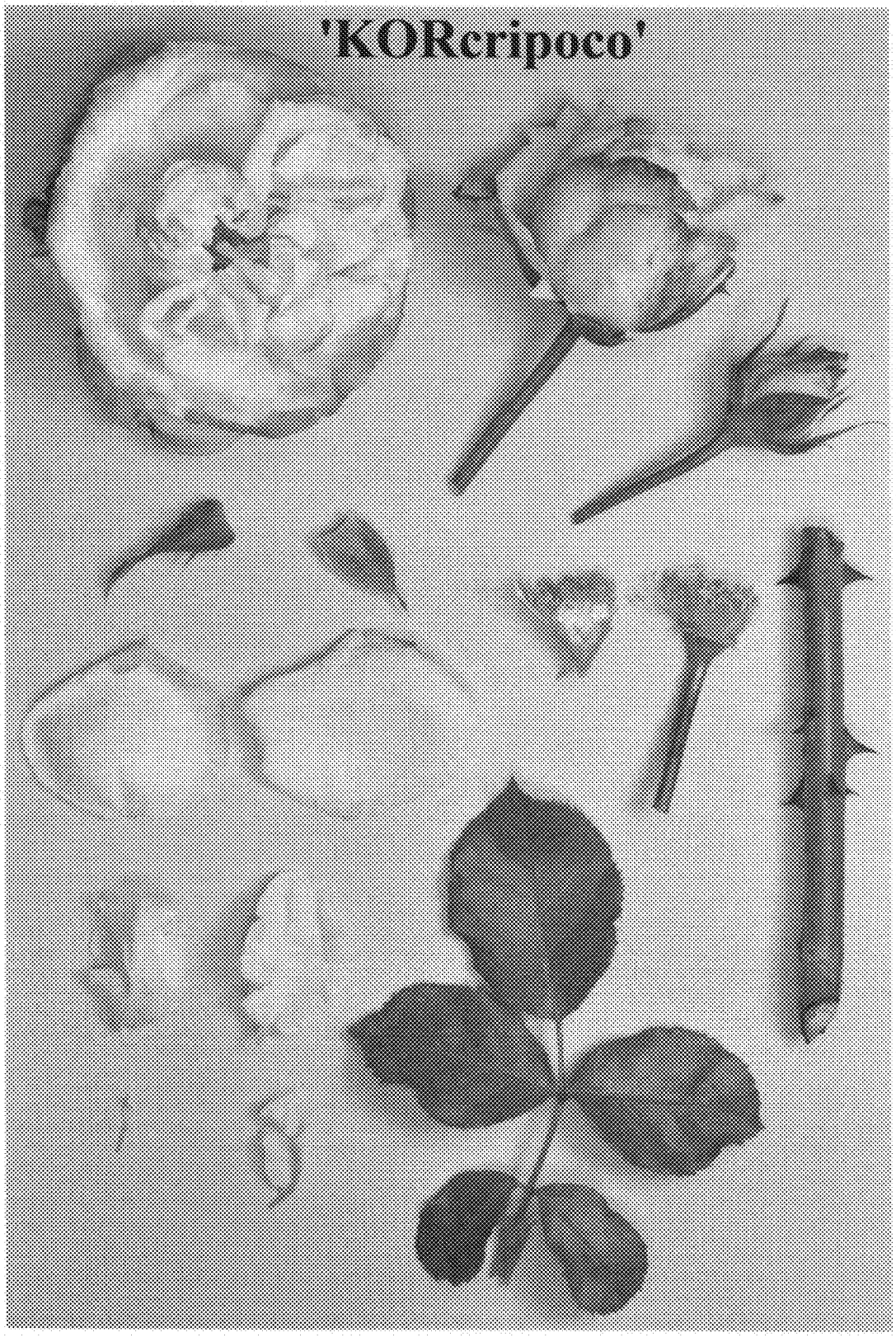
'KORcripoco'